(12) United States Patent
Jackson

(10) Patent No.: US 6,926,737 B2
(45) Date of Patent: Aug. 9, 2005

(54) SPINAL FUSION APPARATUS AND METHOD

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 38 days.

(21) Appl. No.: 10/116,882

(22) Filed: Apr. 5, 2002

(65) Prior Publication Data

US 2002/0116065 A1 Aug. 22, 2002

Related U.S. Application Data

(63) Continuation-in-part of application No. 09/176,708, filed on Oct. 21, 1998, now abandoned.

(51) Int. Cl.$^7$ .................................................. A61F 2/44
(52) U.S. Cl. ................................ 623/17.16; 623/17.11
(58) Field of Search .......................... 623/17.16, 17.11, 623/17.12, 17.13, 17.14, 17.15; 606/61, 69, 60

(56) References Cited

U.S. PATENT DOCUMENTS

| 5,015,255 A | 5/1991 | Kuslich |
| 5,055,104 A | 10/1991 | Ray |
| 5,059,193 A | 10/1991 | Kuslich |
| 5,263,953 A | 11/1993 | Bagby |
| 5,458,638 A | 10/1995 | Kuslich et al. |
| 5,489,307 A | 2/1996 | Kuslich et al. |
| 5,489,308 A | 2/1996 | Kuslich et al. |
| 5,593,409 A | 1/1997 | Michelson |
| 5,609,636 A | 3/1997 | Kohrs et al. |
| 5,658,337 A | 8/1997 | Kohrs et al. |
| 5,683,391 A | 11/1997 | Boyd |
| 5,797,909 A | 8/1998 | Michelson |
| 5,885,287 A | 3/1999 | Bagby |
| 5,904,683 A | 5/1999 | Pohndorf et al. |
| 5,941,880 A | 8/1999 | Errico et al. |
| 5,947,968 A | 9/1999 | Rogozinski |
| 5,980,522 A * | 11/1999 | Koros et al. .................. 606/61 |
| 6,102,948 A | 8/2000 | Brosnahan, III |
| 6,156,037 A * | 12/2000 | LeHuec et al. ............... 606/61 |
| 6,206,922 B1 * | 3/2001 | Zdeblick et al. ......... 623/17.11 |
| 6,325,827 B1 * | 12/2001 | Lin .......................... 623/17.16 |
| 6,432,107 B1 * | 8/2002 | Ferree ......................... 606/61 |
| 6,440,170 B1 * | 8/2002 | Jackson ................... 623/17.16 |
| 6,471,724 B2 * | 10/2002 | Zdeblick et al. ......... 623/17.16 |

FOREIGN PATENT DOCUMENTS

| WO | PCT/US99/01593 | 1/1999 |
| WO | WO 99/38463 | 8/1999 |

* cited by examiner

Primary Examiner—Pedro Philogene
(74) Attorney, Agent, or Firm—John C. McMahon

(57) ABSTRACT

An apparatus for stabilizing and promoting fusion between adjacent vertebrae includes at least a pair of implants to promote bone growth and to fuse with vertebral bone. The implants are joined by a connector. Preferably the implants are inserted into receiving bores in a non-parallel configuration and/or the connector joins the implants so as to bias the implants to a non-parallel configuration. A pair of connecting members also preferably secure the implants to each of the adjacent vertebrae. A method of using the apparatus provides for stabilizing between vertebrae where the original cushioning disc has deteriorated or become damaged. The implants are connected together. Also in the method, the implant receiving bores are non-parallel and/or the implants are biased to non-parallel configurations by joining the implants to the connecting element so as to reduce the inadvertent disturbance of the implants from the receiving bores and to further stabilize the implants overall during the fusion process.

26 Claims, 5 Drawing Sheets

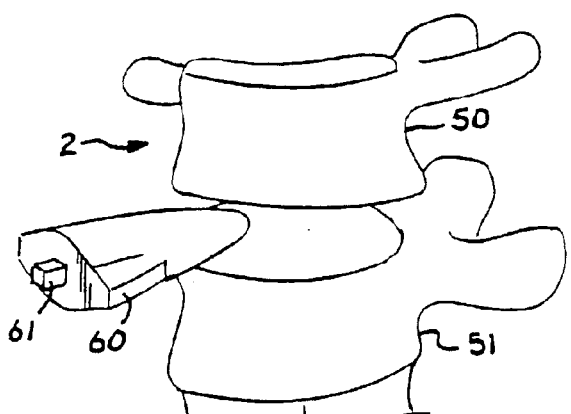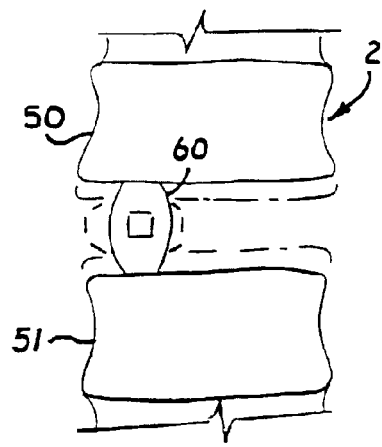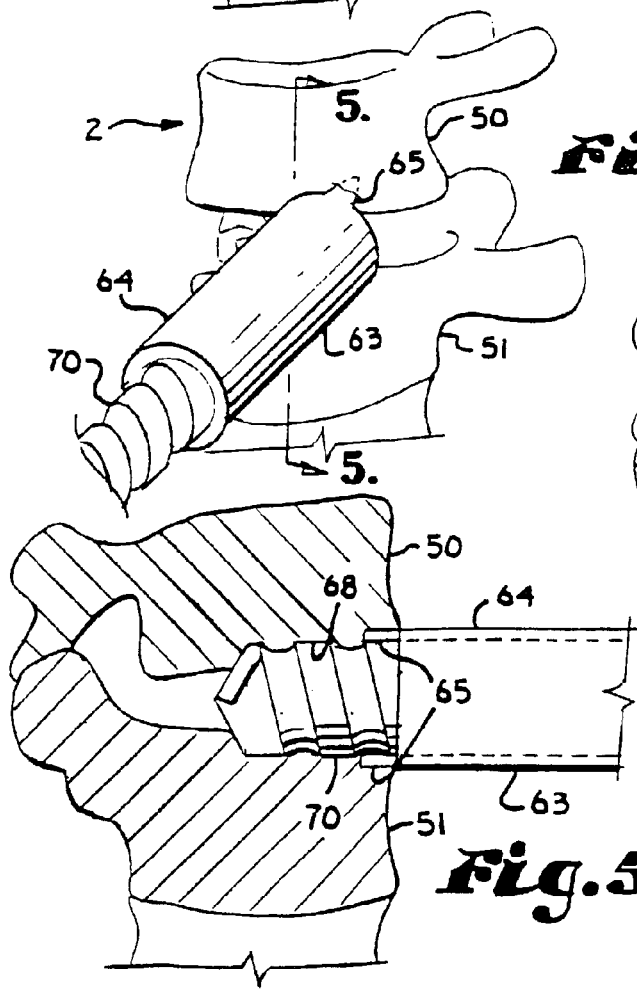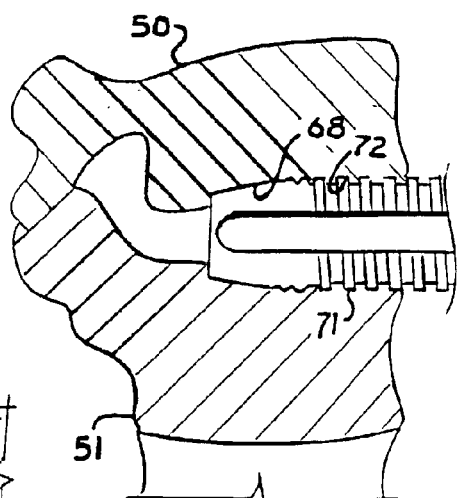

SPINAL FUSION APPARATUS AND METHOD

The present application is one of three related copending applications including application entitled Inflatable MEMS Evaporation Gas Cell Structure System Ser. No. 10/166,882 filed Jun. 11, 2002, application entitled Inflatable Gas Cell Structure Deploying Method, Ser. No. 10/166,881, filed Jun. 11, 2002, and having a terminal disclaimer, and application entitled Inflatable MEMS Ablation Gas Cell Structure System, Ser. No. 10/171,715 filed on Jun. 12, 2002 and having a terminal disclaimer, which three applications all having a common named inventor and all assigned to a common assignee.

BACKGROUND OF THE INVENTION

The present application is directed to an apparatus and method of stabilizing the spine by placement of implants between effected vertebrae which result in fusion of the vertebrae. In particular, the present application is directed to an apparatus and method of improving the stabilization of the implants during the fusion process by linking the implants that are positioned between the same vertebrae together in pairs and also linking the implants to adjacent vertebrae. Still further the apparatus and method provides some pre-loading or twisting of the implants such that the axes of the implants are not parallel, so that the implants are further stabilized relative to their position between the vertebrae and more difficult to inadvertently dislodge. The linking apparatus provides end caps for helping to support the vertebrae against subsidence onto the cages and to resist rotation of the cages.

Many millions of people in the United States alone suffer from some type of spinal injury or disease that effects the spine and especially the discs that are located between adjacent vertebrae of the spine. These discs are necessary to properly position and cushion the vertebrae during the movement. Degeneration, injury or other damage to the disc results in improper alignment of and dysfunction of the vertebrae which often also results in severe pain, the inability to move correctly or to perform certain functions, paralysis and other physical problems which may leave the patient totally incapacitated. Approximately ten percent of the persons who have degeneration or herniation of discs are candidates for surgery to correct the problem. Many different systems have been developed to provide relief to persons having defective discs some of which have been effective and some of which have been relatively ineffective. One of the methods of correcting disc defects has been to properly position the adjacent vertebrae relative to each other and then fuse them together in the proper position or alignment.

Fusing often is best in situations where the discs between the adjacent vertebrae have been either damaged or diseased to such an extent that one or more of the discs no longer functions properly and cannot be preserved by simple procedures such as removal of herniated material and the like.

One particular type of fusion device which requires insertion of an implant having live bone between the vertebrae has grown in substantial popularity in recent years. In this type of implant, two such devices are often inserted in spaced relationship relative to one another between two adjacent vertebrae in the region normally occupied by the defective disc. In order to accomplish this, at least part of the disc is removed or the entire disc is removed (discectomy) and the intervertebral implant devices, often referred to as cages, are inserted in receiving bores. Such implants have exterior walls which are fenestrated, porous or windowed so as to provide multiple openings therethrough. The interior of each of the implants is filled with live bone harvested from another part of the persons body, such as the hip and after implantation, the bone of the vertebrae grows into and joins with the live bone in the implants such that the two adjacent vertebrae and the implant bone grow into a single mass causing a fusion of the two vertebrae so as to hold them in a desired position. While this procedure reduces flexibility of the vertebrae, it significantly reduces pain and/or nerve damage due to collapse, missing or defective discs and, therefore, the benefits outweigh the lost flexibility. This is especially true where the patient would otherwise be immobile.

Applicant, as a spinal surgeon, has found that it is desirable to further stabilize the implants, especially during the period between implantation and the time when stabilizing fusion occurs. Consequently, applicant has developed an apparatus and method of joining a pair of implants that are located between two vertebrae in such a manner as to further stabilize the pair such that they are not as likely to become dislodged at some time before the fusion process is complete or afterward. In addition applicant has found it is desirable to secure implants to vertebrae on opposite sides of the implant and to other implants so as to further improve the stability of those implants. Still further, it has been found desirable to form end caps of the linking structure anterior of the cages to provide additional support to the boney endplate of the vertebrae and also to resist rotation of the cages.

Finally, applicant has found that it is desirable to position the implants such that the central axis of the implants are not parallel to one another prior to joining such that it is more difficult to accidentally remove the implants from bores that receive the implants prior to completion of the fusion process. Yet further applicant has found it desirable to place a slight torque on the implants or preload the implants, such that they are biased against the sides of the bore in opposite directions so as to yet further assist in maintaining the implants between the vertebrae during the fusion process.

SUMMARY OF THE INVENTION

The present invention is directed to implants utilized to stabilize vertebrae wherein the pad or disc between adjacent vertebrae has deteriorated or been damaged and no longer properly spaces and cushions the vertebrae. Implants of the type of the present invention have been previously used to both separate and support adjacent vertebrae while functioning as a promoter for encouraging bone fusion to occur between the vertebrae. The present invention further stabilizes such implants to allow the implants to form a quicker and stronger fusion platform and, very importantly, reduce the risk that the implants will become unseated, such that either surgery is required to repair them, or that the implants will impinge on a nerve, blood vessel, or other structure and produce serious injury either directly or indirectly due to instability of the vertebrae supported by the implants.

In particular the apparatus of the invention includes a pair of implants shaped and sized to be received in a bore or alternatively to be driven by tapping between the vertebrae, each having an axis of insertion and each being placed between two adjacent vertebrae. The implants include a central chamber that receives bone for fusion or material to function as a matrix promoting bone growth and has a plurality of radially located apertures between the chamber and the exterior that allow bone from the vertebrae to grow into and fuse with the bone in the chamber. Alternatively, other types of implants may be used including carbon fiber, porous tantalum or any structure compatible with implantation in the human body and adapted to support bone growth so as to join adjacent vertebrae together through promotion of bone growth and fusion. The implants that are secured into bores preferably include an external rough thread that is sized and shaped to be received in a similar thread in the implant receiving bores to assist in securing the implants in the implant receiving bores.

The implants are joined by a connector. In one embodiment the connector element is an elongate and generally rigid bar of rectangular cross-section that is received in recesses in the front of each implant and secured thereto by fasteners. Preferably, the connector is not aligned to be perpendicular to the central axis is slightly bowed at an angle preferably between about 2° to 10°. This allows the implants to be biased relative to each other such that the implants are non-parallel after completion of the implantation. This urges and preloads the implants into the sidewalls of the implant receiving bores, which may also be non-parallel, and makes it more difficult for the implants to be unintentionally disturbed while in the implant receiving bores or pulled entirely from the bores.

In a second embodiment the connecting element is a relatively thin plate connecting the implants and also preferably designed to allow the implants to be aligned to be non-parallel. The plate also includes at least one elongate slot so that upon installation, a set screw can slide along the plate during tightening while effectively biasing the implants against the wall of the implant receiving bores.

In a third embodiment a connecting plate joins two tap-in type intervertebral implants. To gain additional stability a pair of L-shaped connecting plates are secured to the implants near one end thereof and to the adjacent vertebrae. Also the implants between different vertebrae are joinable by a connecting strip.

In a preferred embodiment the connector is joined to a pair of end caps with one end cap positioned directly anterior of a respective cage. Each end cap has upper and lower surfaces which are elongate and sized and positioned to support the anterior endplate of each vertebrae when the apparatus is fully assembled. The end caps resist subsidence of the vertebrae onto the cages and also resist rotation of the cages. Also, preferably the end caps extend outward sideways relative to the top and bottom of each cage, so as to help support the vertebrae on either side of the cages.

OBJECTS AND ADVANTAGES OF THE INVENTION

Therefore, the objects of the present invention are: to provide a spinal stabilizing system having an apparatus including implants that are positioned in bores between vertebrae having a degenerated or damaged disc wherein the implants include live bone or are constructed of bone growth enhancing material for generating fusion between the vertebrae and wherein the implants are joined for greater stabilization during the fusion process; to provide such an apparatus that provides for proper spacing and alignment between the vertebrae thereby relieving pressure on nerves, restoring strength to the spinal column and correcting other problems associated with vertebrae misaligned due to disc failure or related damage; to provide such an apparatus including structure to further join implants to adjacent vertebrae above and below the implants and other implants so as to additionally improve stabilization of the implant during the fusion process; to provide anterior end caps for each cage that support the anterior endplate of vertebrae spaced by the cages, so as to resist subsidence of the vertebrae onto the cages and to resist rotation of the cages; to provide such an apparatus wherein the implants are joined in such a manner that the axes thereof are nonparallel so as to substantially reduce the likelihood of accidental dislodgement of the implants from the bores in which they are seated or their correct position between the vertebrae; to provide such an apparatus where the implants are biased against the interior walls of the bores so as to further reduce the likelihood of inadvertent removal of the implants from the bores during the fusion process; to provide a method that utilizes the implants in such a manner as to provide an extremely stable implant construction during the fusion process to reduce the likelihood of disturbance of the implants or of accidental removal of the implants from the bores and to speed the fusion process so as to quickly stabilize the patient's spine; and to provide such an apparatus and method which are relatively simple to use, economical to produce and utilize and that are especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is a perspective view of the patients spine prior to insertion of the implants illustrating the insertion of a non-circular spacer between the vertebrae.

FIG. 3 is a front view of the vertebrae of the patients spine showing the spacer in phantom lines as the spacer was inserted and showing the vertebrae in phantom lines at the time of first insertion of the spacer and also showing the spacer in solid lines as the spacer is rotated to space the vertebrae that are shown in solid lines, when spaced.

FIG. 4 is a perspective view of the patients spine illustrating the pair of vertebrae in spaced relationship to one another and illustrating a bore being produced by use of a drill and drill guide.

FIG. 5 is a fragmentary cross-sectional view of the spine illustrating an implant receiving bore being drilled, taken along line 5—5 of FIG. 4.

FIG. 6 is a fragmentary cross-sectional view of the spine illustrating a top threading the implant receiving bore, taken along line 5—5 of FIG. 4.

DETAILED DESCRIPTION OF THE INVENTION

Figure 1:
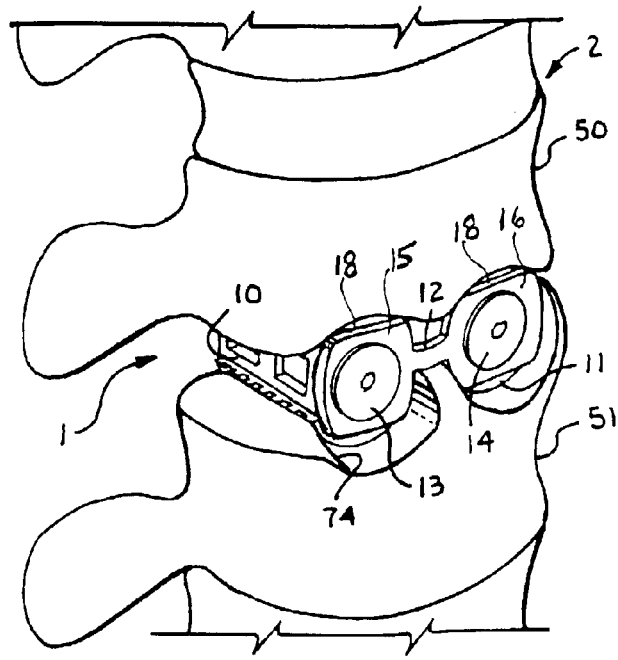
FIG. 1 is a fragmentary perspective view of a patient's spine showing implants in accordance with the present invention inserted in a region normally occupied by a disc between two vertebrae wherein the implants are joined to each other by a stabilizing structure or apparatus according to the present invention.
Figure 7:
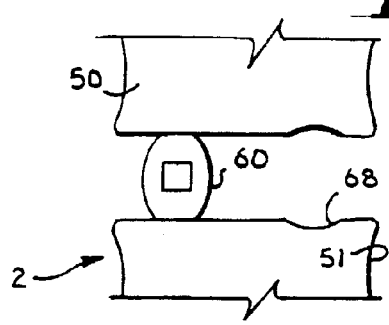
FIG. 7 is a front view of the patient's spine subsequent to the production of an implant receiving bore by the steps of FIGS. 2 through 6.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally represents a first embodiment of a spinal stabilization and fusion enhancing apparatus or system 1 in accordance with the present invention shown in FIGS. 1 and 8 through 11a and showing installation of the apparatus 1 in FIGS. 1 through 11a in the spine 2 of a patient.

The fusion enhancing apparatus 1 includes a pair of bone receiving cages or implants 10 and 11 that are joined to a connecting plate 12 that joins a pair of end caps 15 and 16 by a pair of set screws 13 and 14 respectively.

The implants 10 and 11 are designed to be received in a circular bore, but have a somewhat rectangular cross-section with arcing at four opposite corners. Implants of the type illustrated are sold in the marketplace by Spine-Tech Inc. and other manufacturers of spinal fusion type implants. It is foreseen that pairs of implants of a wide range of shapes and constructed of a wide range of materials may be utilized in the invention, provided that the implants are positionable between adjacent vertebrae, that is, intervertebral implants; are compatible with use in the human body; promote, encourage or enhance bone growth into the implant or between the vertebrae and are connectible.

Each of implants 10 and 11 (best seen in FIG. 11) are elongate and have a central axis A. Each of the implants 10 and 11 also are somewhat annular in shape having a central chamber 20, surrounded by a wall 21 having an outer surface 22. The wall 22 is penetrated by a plurality of ports or windows 26 that are radially positioned and open into the central chamber 20. The outer surface 22 also includes partial threads 27 interspaced at opposite corners with the windows 26.

Each implant 10 and 11 has an enclosed rear end 30 and an anterior or front end 31. The implant front end 31 has a threaded bore 32 that is generally aligned with the axis A and an outer generally planar surface 33. When installed, bone chips 35, normally harvested from another part of the body such as the hip, are inserted in the chamber 20 (see FIG. 8).

The plate 12 is relatively rigid, but has a slight amount of resiliency. The plate 12 joins two spaced end caps 15 and 16 having loops 40 and 41 respectively joined by a connector 42. The end caps 15 and 16 are sized and shaped to generally sit snugly against the front end surface 33 of each of the implants 10 and 11 so as to be located at least partially directly anterior of a respective implant 10 and 11. The interior of each illustrated loop 40 and 41 is somewhat oblong. The oblong nature of the loops 40 and 41 is necessary in some cases to allow for various spacing of the implants 10 and 11 and more importantly to allow the second of the set screws 13 or 14 to be started into the associated bore 32. It is foreseen that in certain embodiments the loops 40 and 41 would not be required to be oblong, but could be circular or the like.

Figure 11:
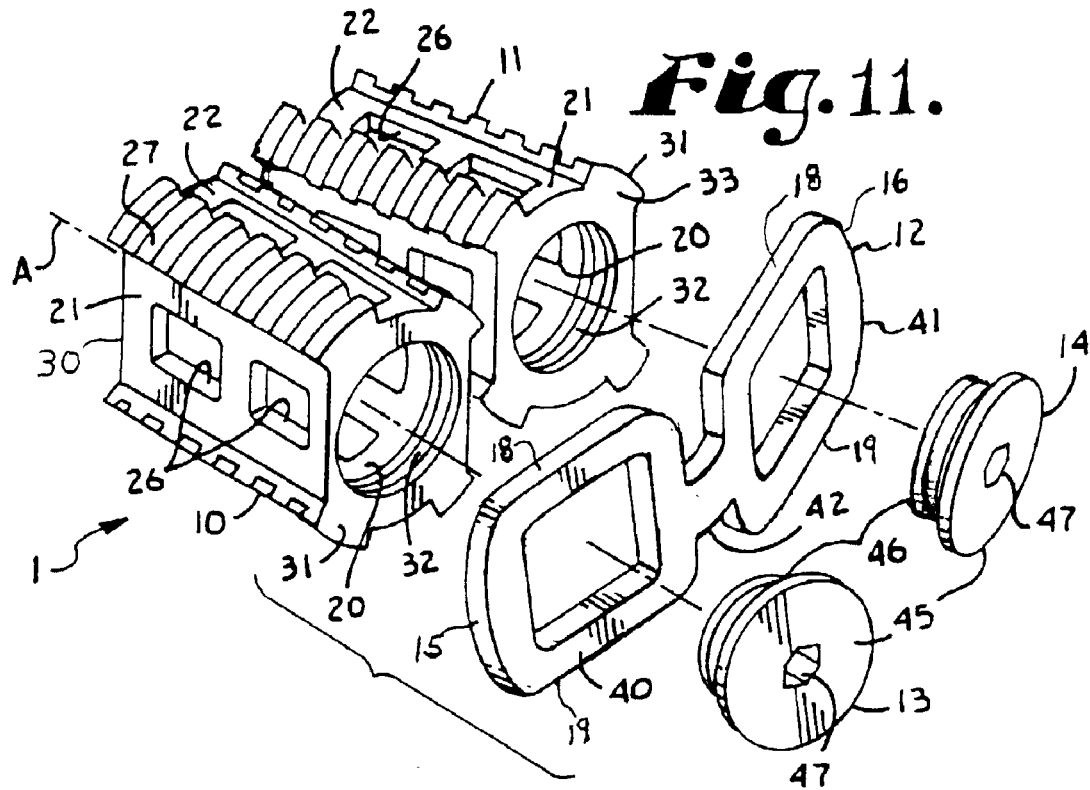
FIG. 11 is an exploded and enlarged perspective view of the implants and a connecting element prior to joining of the implants.
Figure 11A:
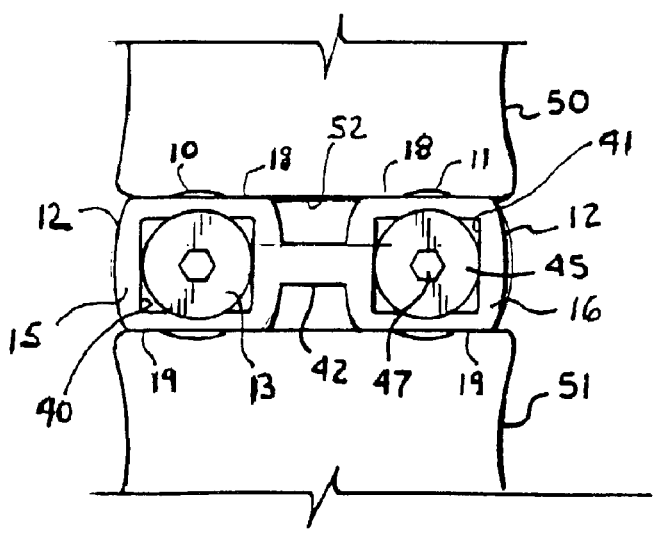
FIG. 11a is a front elevational view of the implants and connecting apparatus, shown in FIG. 11, on a reduced scale and mounted between a pair of spinal vertebrae.

The end caps 15 and 16 each having a respective generally flat, thick and elongate upper surface 18 and lower surface 19. The surfaces 18 and 19 being generally parallel and being sized and shaped, such that when the entire apparatus 1 is assembled in a patient between vertebrae 50 and 51, such as is shown in FIG. 11a, the surfaces 18 and 19 engage facing interior endplate surfaces 52 and 53 of respective vertebrae 50 and 51, so as to provide additional support to the vertebrae 50 and 51 and so as to resist subsidence of the vertebrae 50 and 51 with respect to the implants 10 and 11. The end caps 15 and 16 are sized to be positioned between the implants 10 and 11 and the most forward or anterior part of the vertebrae 50 and 51. Because the end caps 15 and 16 are secured to a respective implant 10 and 11 so as to resist rotation therebetween and because the surfaces 18 and 19 are elongate and abut the vertebrate surfaces 52 and 53, the end caps 15 and 16 also help to resist rotation of the generally roundish implants 10 and 11, so that the implants are less likely to unscrew from between the vertebrae 50 and 51 after assembly, as described below. As is shown in FIG. 11a, the end caps 15 and 16 extend out sideways to either side of the implants 10 and 11 at the top and bottom of the implants 10 and 11 in the region where the implants 10 and 11 engage the vertebrae 50 and 51, so as to provide extra support in that region.

Figure 10:
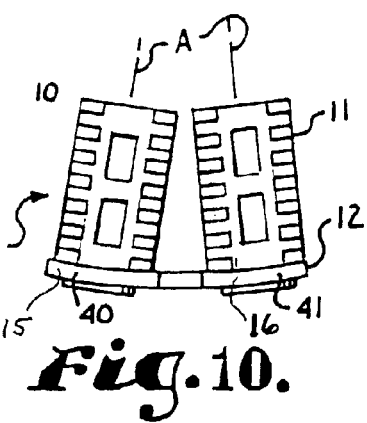
FIG. 10 is a schematic top plan view of the pair of implants subsequent to joining of the implants.

As is seen in FIG. 10, when the apparatus 1 is assembled, the end caps 15 and 16 abut directly against the anterior end of respective implants 10 and 11. In this manner the end caps 15 and 16 are directly anterior of the implants 10 and 11 and extend outward from the implants 10 and 11 on each side thereof. Each end cap 15 and 16 is preferably also wider from side to side as compared from top to bottom, as seen in FIG. 11a, so as to resist rotation or instability. That is, the surfaces 18 and 19, as well as any projections therefrom, extend along and are in touching relationship with the vertebrae on either side of respective implants. While the surfaces 18 and 19 illustrated herein are generally flat, it is foreseen that in some embodiments of the invention the upper and lower surfaces of the end caps may be shaped to closely or almost exactly follow the contour of the base of the vertebrae against which the surfaces rest. In particular, the upper and lower surfaces of the end caps could have a central hump or rise to follow the cage receiving bore and/or may be slopped from anterior to posterior to follow the slight concavity associated with such vertebral surfaces.

In the present embodiment the end caps 15 and 16 form the plate 12 with the connector 42. The plate 12 is bowed or bent from top to bottom across the connector 42. Normally, the angle of the bend will be in the range of 2° to 10° and, in the illustration the angle is about 7° and the bend can be seen in FIGS. 9 and 10. It is foreseen that the end caps 15 and 16 can be non-integral of the connector or may be used independently from the connector, when the connector is not needed or desired.

The plate 12 is relatively rigid to hold the implants 10 and 11 in a non-parallel relationship to each other as seen in FIG. 10 to make the implants 10 and 11 harder to disturb once implanted and to also provide a slight loading or bias to the implants 10 and 11 in some instances to further stabilize the apparatus 1.

The set screws 13 and 14 are sized and shaped to be received through the connector 42 loops 40 and 41 respectively with a head 45, that is larger in diameter than the loops 40 and 41, abutting on and snugged against each respective loop 40 and 41. Each set screw includes a threaded surface 46 below the head 45 that is operably received in a respective implant mainly threaded bore 32. Each head 45 also includes an opening 47 sized and shaped to receive a driving tool such as an allen wrench, screwdriver or the like (not shown).

In use, the patient's spine 2 is exposed and the pair of vertebrae 50 and 51, having facing surfaces including anterior surfaces 52 and 53 respectively, are surgically exposed, normally by entry from the front of the patient. Although rear entry is possible, front entry is normally considered to be preferred to rear entry.

The vertebrae 50 and 51 to be stabilized and fused are first separated, since proper spacing has usually been compromised by a defective intervertebral disc or vertebrae damage. To space the vertebrae 50 and 51 a nonsymetrical spacer having a rotating lug 61 is inserted between the vertebrae 50 and 51 on the left or right side (see FIG. 2).

The spacer 60 is then rotated (as seen in FIG. 3) and the vertebrae 50 and 51 are further spaced as illustrated by the difference between phantom lines (not spaced) and solid lines (spaced) in FIG. 3. Normally the vertebrae 50 and 51 are spaced approximately to the limits of ligaments (not shown) holding the vertebrae 50 and 51 together.

A guide tool 63 is then positioned opposite the spacer 60, as seen in FIGS. 4 and 5. The guide tool 63 includes a tube 64 with pins 65 at one end to provide better gripping of the bone. The guide tool 63 aligns the location of a bore 68 to receive one of the implants 10 or 11. A drill bit 70 is inserted in the guide tool sleeve 64 and the bore 68 is drilled. The drill bit 70 is then removed and a threading tool 71 is inserted to form a coarse thread 72 on the interior of the bore 68 that mates with the thread 27 of implants 10 and 11.

The threading tool 71 is removed from the bore 68 and an implant 10 (see FIG. 8) is inserted. The spacer 60 is then removed and the drilling and threading procedure is repeated on the opposite side creating a second bore 74. The second implant 11 is then inserted in the second bore 74, as seen in FIG. 1.

Figure 9:
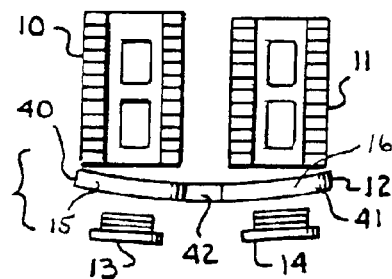
FIG. 9 is a schematic top plan view of a pair of implants prior to joining of the implants.
Figure 8:
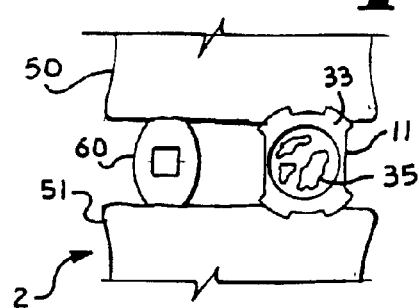
FIG. 8 is a front view of the patient's spine showing an implant positioned in the bore formed in steps of FIGS. 2 through 7.

The connecting plate 12 is then attached to the implants 10 and 11 using the set screws 13 and 14. The implants 10 and 11 may originally be parallel as shown in FIG. 9 or the bores 68 and 74 may be drilled to be non-parallel. In either case, when the plate 12 is secured to the implants 10 and 11 (shown schematically in FIG. 10), the implants 10 and 11 are urged into a non-parallel alignment due to the angle of the bores 68 and 74, the loading of the plate 12 or both.

In particular, the set screw 13 is first placed to extend through the loop 40 into the bore 32 of implant 10 and tightened. The second set screw 14 is likewise positioned with respect to implant 11. As the set screw 14 is tightened the bend in the plate 12 biases the implants 11 and 12 to a non-parallel alignment.

It is noted that the bores 68 and 74 may also be skewed (not in the same horizontal plane) to give the implants greater gripping and purchase with respect to the vertebrae 50 and 51, such that the implants 10 and 11 are more likely to resist forces that try to displace the implants 10 and 11 during use.

Figure 13:
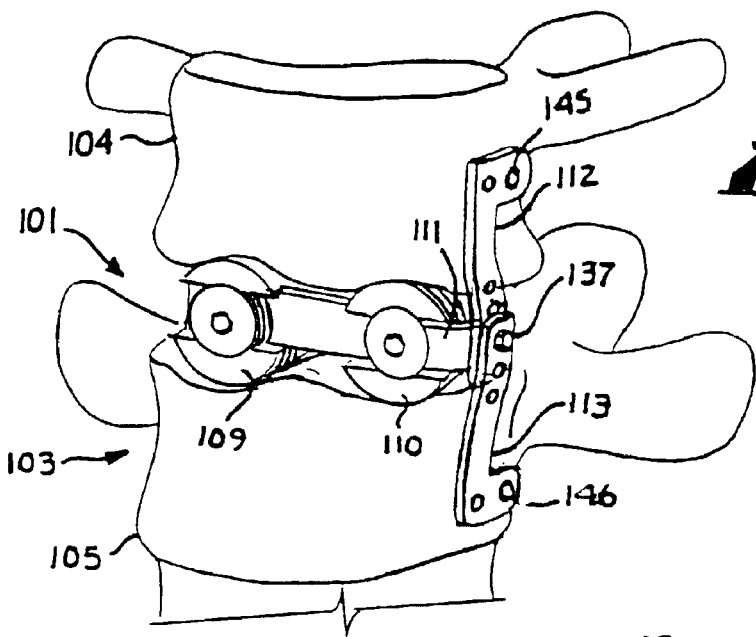
FIG. 13 is a fragmentary perspective view of the first modified implant system positioned in a patient's spine between two vertebrae and inter-connecting the vertebrae to the system.
Figure 12:
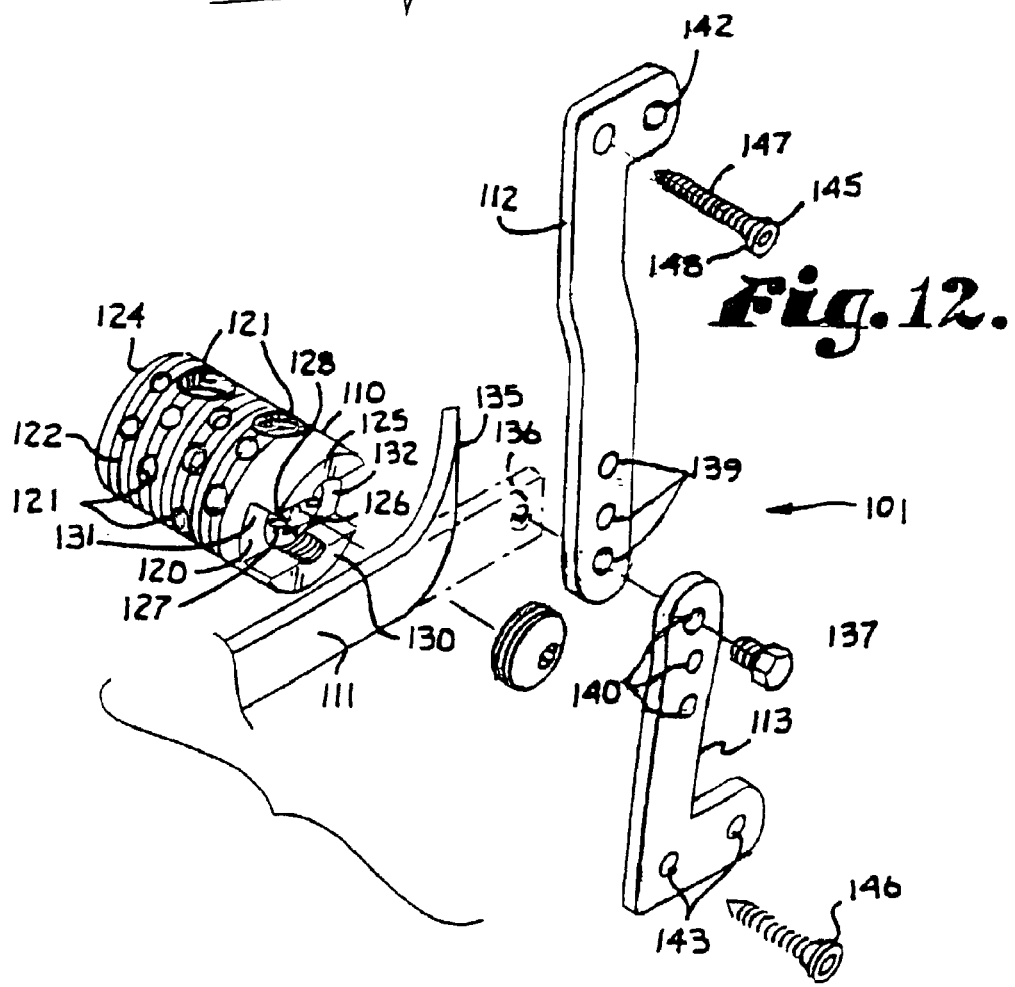
FIG. 12 is a perspective view of a portion of a first modified implant system showing an implant, a rod for connecting the implants and a pair of links for connecting the implants to adjacent vertebrae.

The reference numeral 101 generally represents a modified stabilization apparatus or system that is illustrated in FIGS. 12 and 13. The system 101 which is seen installed in a spinal column 103 of a patient in association with and at least partly between a pair of vertebrae 104 and 105.

Individual elements of the stabilization system 101 are illustrated in FIG. 102. The system 101 includes a pair of bone receiving and engaging cages or implants 109 and 110, a connecting element or bar 111 and a pair of connecting members 112 and 113.

Each of the implants 109 and 110 is cylindrical in shape having an annular wall 120. Each wall 120 is porous or heavily fenestrated and includes a plurality of pass through bores or apertures 121 that are generally radially aligned. The exterior of each of the walls 120 also includes a rough helical thread 122 that is aligned with a central axis of each respective implant 109 and 110 and which is designed to help secure each respective implant 109 and 110 in a desired position thereof.

Each of the implants 109 and 110 includes a rear end 124 for closing the rear end and has a front end 125 that opens into an interior bore 126. An interior chamber 127 is thus formed between the annular wall 120 and the end cap 125 that is not entirely enclosed as it opens outwardly through the various apertures 121.

The chamber 127 receives bone fragments 128 that are harvested from another part of the patient's body, such as the patient's hip. The front end 125 of each implant 109 and 110 includes a rectangularly shaped recess sized and shaped to receive the connecting element, plate or bar 111. The recess 131 has a partial rear wall surface 132. The bar 111 is not linear but has a bend or curve in the range of 2° to 10°, preferably about 5°. This same feature may be created by a continuous curve or arc located between the implants 10 and 11. In this manner, when the connecting bar 111 is placed in the recess 131 and abuts against the surface 132, the two implants 109 and 110 are urged to align in a slightly nonparallel relationship to one another, preferably so as to toe in or converge at the rear ends 124 of the implants 109 and 110 opposite the bar 111.

It is foreseen that the axial deviation of the two implants 109 and 110 could also be spread further apart in the rear thereof as opposed to where the implants 109 and 110 join the bar 111, that is diverge or toeout. On the other hand, the implants 109 and 110 may be aligned to also be skewed relative to one another and/or divergent or convergent.

The connecting bar 111 is bent on one outer wing 135 thereof to conform to the curvature of the vertebrae 104 and 105, as shown in FIG. 12. The wing 135 extends outwardly further than the opposite side of the bar 111 and is normally located on the left hand side of the patient. The wing 135 is so located, as surgeons normally enter from the front, but on the left side, so that the patient left hand location allows the surgeon better access.

Located in the wing 135 is a threaded bore 136 that receives a mating screw 137. The screw 137 is also received through one of a series of apertures 139 and 140 in each of the connecting members 112 and 113.

The connecting member 112 and 113 are L-shaped and each have a second set of threaded apertures 142 and 143 spaced from the wing 135 and positioned opposite the bones 104 and 105 respectfully as shown in FIG. 13. The bone screws 145 and 146 are of the type having a thread 147 on the body for taping into bone and a second thread 148 on the head that is mated with the bores 142 and 143 respectfully.

The modified apparatus 101 is installed and functions in a similar manner to the apparatus 1 of the previous embodiment with the principal exception that the connecting members 112 and 113 are secured to the adjacent vertebrae 104 and 105 so as to secure the apparatus 101 directly to the vertebrae 104 and 105.

Figure 14:
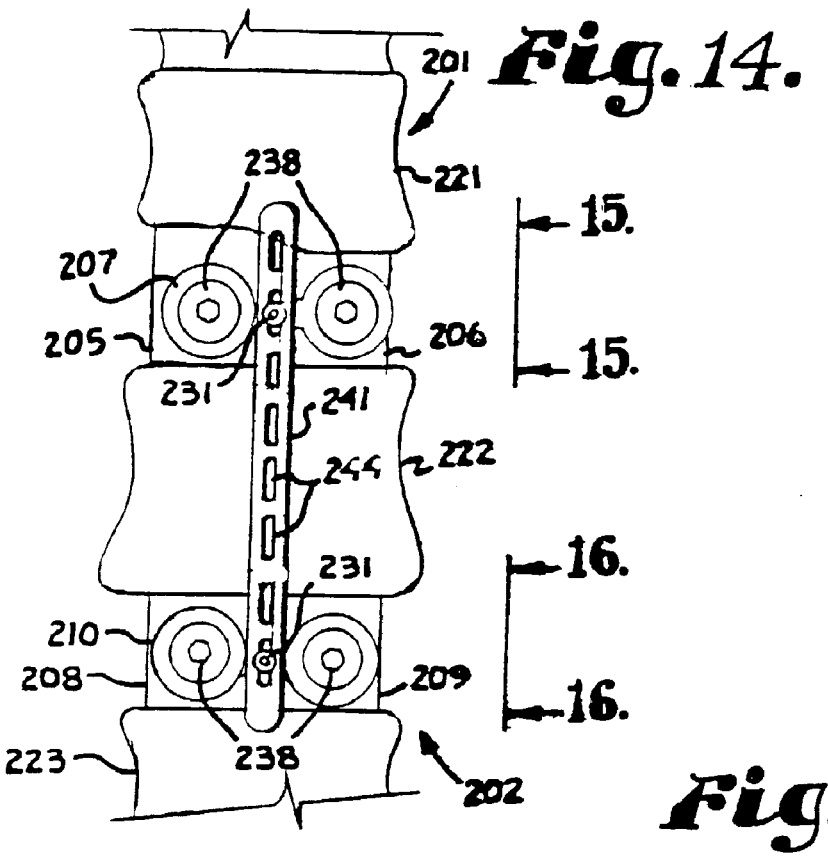
FIG. 14 is a front elevational view of a second modified implant system showing two pairs of top-in implants with connectors and a strip joining the connectors.
Figure 15:
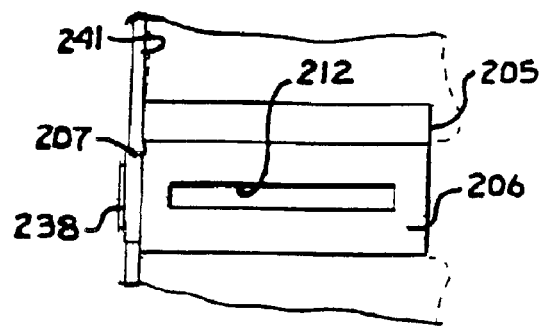
FIG. 15 is a side elevational view of the upper pair of implants of FIG. 14, taken along viewing line 13—13.
Figure 16:
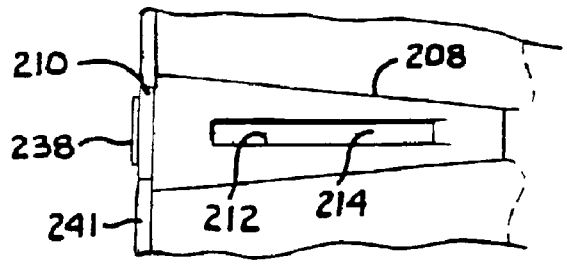
FIG. 16 is a side elevational view of the lower pair of implants of FIG. 14, taken along viewing line 14—14.

Illustrated in FIGS. 14, 15 and 16 is a second modified embodiment of a spinal stabilization apparatus in accordance with the invention, generally identified by the reference numeral 201 and used in conjunction with a spine 202.

The apparatus 201 includes a first pair of implants 205 and 206 joined by a first connecting member 207 and a second pair of implants 208 and 209 joined by a second connecting member 210. The implants 205, 206, 208 and 209 are similar to the implants of the previous embodiments in that each contains bone and has windows 212 or similar openings extending between an interior chamber holding the bone and an exterior.

The implants 205, 206, 208 and 209 are different in comparison to those of the previous embodiment in the shape and method of implantation thereof. The implants 205, 206, 208 and 209 illustrate implant types that are placed between bones 220, 221 and 222 by striking or pushing, sometimes referred to as tap-in type herein, as opposed to being secured by screwing into previously formed bores. Consequently, the implants 205, 206, 208 and 209 have a rectangular cross section as opposed to circular or near circular cross section.

The implants 205, 206, 208 and 209 illustrate several different types. In particular the implants 205 and 206 are each generally rectangular when viewed from the side (see FIG. 15), but have different heights with implant 205 being larger than implant 206. The implants 205 and 206 are used to support opposite sides of a bone 221 that has deteriorated or been damaged on the side requiring the larger implant 205 to level the opposite sides of the bone 221.

The implants 208 and 209 have a trapezoidal configuration when viewed from the side (see FIG. 16) to operably space the front of the bones 222 and 223 more than the rear thereof.

The connector plates 207 and 210 are similar to the connector plate 12 of the first embodiment and join the implants 205 and 206 as well as the implants 208 and 209 respectively with the one difference being that the plates 207 and 210 each include a centrally located threaded bore 230 that receives a threaded screw 231. Each of the connector plates 207 and 210 are joined to respective implants 205, 206, 208 and 209 by set screws 238.

An elongate strip 241 operably extends vertically along the front of the spine 202 and joins the connecting plates 207 and 210. The strip 241 has a series of oval shaped apertures 244 that receive screws 231 so as to secure the strip 241 to each plate 207 and 210 and so as to further stabilize the apparatus 201 and spine 202.

The apparatus 201 is installed in a somewhat different manner than that of the previous embodiments. Instead of forming bores to receive the implants, any pad between bones 221, 222 and 223 is removed and the implants 205, 206, 208 and 209 are driven into place by tapping or the like. The connecting plates 207 and 210 are then joined to respective implants 205, 206, 208 and 209 by set screws 238, as in the previous embodiments, with the plates 207 and 210 bent to a selected angle. The strip 241 is then joined to each connecting plate 207 and 210 by screws 231.

While the implants have mainly been described as cages for receiving bone to enhance bone growth into the cages and to fuse the vertebrae, it is foreseen that other types of implants may be used for this purpose. For example, carbon fiber implants, implants of porous tantalum and other structures of stainless steel, tungsten and other body friendly materials, either coated with bone growth enhancing medium or simply porous so as to support and encourage bone growth into and through the implants, may be utilized in accordance with the invention.

It is to be understood that while certain forms of the present invention have been illustrated and described herein, it is not to be limited to the specific forms or arrangement of parts described and shown.

What is claimed and desired to be secured by Letters Patent is as follows:

1. An end cap for a spinal implant for operative positioning between a pair of vertebrae in a patient; said end cap being sized and shaped to be operatively positioned directly anterior of the implant so as to extend between and be in touching relationship with the vertebrae; said end cap having elongate upper end lower surfaces that extend outwardly on opposite sides of the implant during use so as to operatively support the vertebrae on opposite sides of the implant; said surfaces being sized and shaped to abut directly against facing surfaces of the vertebrae at the anterior end of the vertebrae during use so as to resist subsidence of the vertebrae relative to the implant.

2. The end cap according to claim 1 wherein:
   a) said end cap is sized and shaped to abut directly against the implant during use.

3. The end cap according to claim 1 including a fastener wherein:
   a) said end cap is secured to the implant by said fastener during use so as to snug said end cap against the implant and to frictionally resist rotation of the implant after installation.

4. The end cap according to claim 1 in combination with the implant and a fastener to secure said end cap to said implant.

5. In a screw-in type spinal implant apparatus having an implant wherein the implant is positioned between a pair of vertebrae for promotion of stability and fusion between the vertebrae, the improvement including:
   a) an end cap sized and shaped to be positioned directly anterior of the implant during use and having upper and lower elongate surfaces that extend outwardly on either side of the implant during use;
   said end cap surfaces being sized and shaped to directly engage and support facing surfaces of the vertebrae at an anterior end of the vertebrae so as to provide support to the vertebrae during use and resist subsidence of the vertebrae relative to the implant.

6. The apparatus according to claim 5 wherein:
   a) during use said end cap upper and lower surfaces extend outwardly to the sides beyond the implant in the region whereat the implant engages the vertebrae.

7. An apparatus for stabilizing between adjacent vertebrae of a spine by promotion of bone fusion between the adjacent vertebrae; said apparatus comprising:

a) a pair of fusion implants adapted to be received in spaced side by side relationship between a pair of adjacent vertebrae; each of said implants adapted to promote bone growth between the adjacent vertebrae; and b) a connector extending between and joined to each of said implants, such that said implants are spaced but operably stabilized in use; said connector including first and second end caps; said first and second end caps each being sized and shaped so as to be located adjacent to and anteriorly of respective implants in use; at least one of said end caps having upper and lower surfaces sized, shaped and positioned during usage to directly engage and extend along respective facing surface portions of adjacent vertebrae near anterior ends of the vertebrae and outwardly on either side of a respective implant during usage so as to resist subsidence of the vertebrae relative to the implants.

8. The apparatus according to claim 7 wherein:

a) said connector is a substantially rigid elongate bar; and including b) one fastener securing each of said end caps to respective implants.

9. The apparatus according to claim 8 wherein:

a) each of said implants has a recess located at a front end thereof; said bar being received in both of said recesses.

10. The apparatus according to claim 9 wherein:

a) said bar is bent at an angle between 2° and 10°, such that when said bar is received in said recess, said implants are biased so that the central axes thereof are nonparallel.

11. The apparatus according to claim 7 wherein:

a) said connector is a plate integrally joining said end caps and operably joined to the front end of each of said implants during usage.

12. The apparatus according to claim 11 wherein:

a) said plate is bent intermedially between said end caps and is secured to said implants such that said implants are biased in such a manner that central axes associated with said implants are nonparallel when assembled.

13. The apparatus according to claim 7 wherein:

a) each implant has a front end that has a pass through bore that is threaded; and b) said fasteners comprise set screws operably joining said end caps to said implants and being received in said threaded bore.

14. An apparatus for stabilizing intervertebrally by promotion of bone fusion between two adjacent vertebrae of a spine; said apparatus comprising:

a) a pair of implants adapted to be both received between the pair of adjacent vertebrae; each of said implants having an interior chamber for receiving bone fragments; and each of said implants having a plurality of radially positioned and wall penetrating apertures adapted to allow bore fragments in said bores to join and fuse with bore in the adjacent vertebrae; said implants being operably used in side by side but spaced relationship to one another;

b) a connecting member operably extending between and joined to each of said implants said connecting member being joined to an anterior end of each implant; said connecting member including structure that is sized and shaped to be positioned adjacent to and directly anterior to at least one of said implants; said connecting member including an end cap with upper and lower elongate and vertebral engaging surfaces that are sized, shaped and positioned to engage facing portions of the vertebrae on opposed lateral sides of such one implant during use so as to resist subsidence of the vertebrae relative to said one implant; and c) fasteners operably securing said connecting member to each of said implants.

15. A method of stabilizing and promoting bone fusion between two adjacent vertebrae comprising the steps of:

a) selecting a pair of implants with each implant adapted to promote bone growth;

b) forming a pair of implant receiving bores between the two adjacent vertebrae with each of the implant receiving bores sized to snugly receive a respective one of said implants such that both implants are between the same pair of vertebrae;

c) placing said implants in side by side but spaced relationship relative to one another in respective bores;

d) joining a front end of each implant with a connector such that said implants are spaced, but joined and stabilized by said connector; and e) placing end caps directly anterior of each implant; each of said end caps including structure that is sized and shaped so as to be positioned adjacent to an anterior end of at least one of said implants during use and so as to directly contact and extend along facing surface portions of the vertebrae on opposed sides of said one implant to resist subsidence of said vertebrae relative to said one implant.

16. The method according to claim 15 including the step of:

a) prior to the step of forming said implant receiving bores, biasing apart said two adjacent vertebrae to the extent allowed by connecting ligaments.

17. The method according to claim 16 wherein said biasing is performed by:

a) inserting a non-circular plug between said vertebrae in a first alignment and then rotating said plug to space said vertebrae.

18. The method according to claim 15 including:

a) forming said implant receiving bores such that the central axes thereof are non-parallel.

19. The method according to claim 18 wherein:

a) said implant receiving bores diverge from front to rear.

20. The method according to claim 15 including the step of:

a) joining said implants to said connector in such a manner that central axes of each of said implants is in a non-parallel configuration relative to each other and held in such configuration by said connector.

21. The method according to claim 15 including the step of:

a) selecting a connecting member and securing said member to said implants and to one of said adjacent vertebrae by a fastener.

22. The method according to claim 21 wherein:

a) said member is a first member and including the step of selecting a second member and then securing said second member to said implants and to the second of said adjacent vertebrae.

23. In an apparatus for promoting fusion between adjacent vertebrae including a pair of intervertebral implants; the improvement comprising:

a) joining said implants with a connecting member having a pair of end caps that are each operably positioned directly anterior of said implants during usage; said end caps each including upper and lower elongate surfaces sized and shaped to directly engage facing surface portions of the vertebrae; said end caps being further sized and shared to extend outwardly on opposed sides of a respective implant along and in touching relation to opposed facing vertebral surfaces so as to operably support the vertebrae in cooperation with the implants in the region of the implants.

24. The apparatus according to claim 23 wherein:

a) said connecting member is bent such that said implants are urged to a non parallel alignment relative to each other.

25. An apparatus for stabilizing between adjacent vertebrae of a spine by promotion of bone fusion between the adjacent vertebrae; said apparatus comprising:

a) a pair of implants adapted to be received in side by side relationship between a pair of adjacent vertebrae; each of said implants adapted to promote bone growth between the adjacent vertebrae;

b) each of said implants having a recess located at a front end thereof;

c) a connector joined to and extending between each of said implants during usage; said connector being a substantially rigid elongate bar; said bar being bent at an angle between 2° and 10°, such that, when said bar is received in said recess, said implants are biased so that the central axes thereof are nonparallel; and d) said bar being received in both of said recesses; and e) a pair of end caps each being operably positioned directly anterior relative to a respective implant during use and having opposed spaced upper and lower surfaces that are sized and shaped to extend along and in direct touching relationship with respect to facing surfaces of opposed vertebrae and so as to provide support to facing surface portions of the vertebrae; said end caps extending outwardly on opposed sides of respective implants along vertebral surfaces during usage.

26. An apparatus for stabilizing between adjacent vertebrae of a spine by promotion of bone fusion between the adjacent vertebrae; said apparatus comprising:

a) a pair of fusion implants adapted to be received in spaced side by side relationship between a pair of adjacent vertebrae; each of said implants adapted to promote bone growth between the adjacent vertebrae;

b) a connector extending between and joined to each of said implants, such that said implants are spaced but operably stabilized in use; said connector being a substantially rigid elongate bar;

c) each of said implants has a recess located at a front end thereof; said bar being received in both of said recesses during usage;

d) said bar is bent at an angle between 2° and 10°, such that when said bar is received in said recess, said implants are biased so that the central axes thereof are nonparallel;

e) fasteners securing said connector to each of said implant; and f) a pair of end caps with each end cap mountable on one end of a respective implant; each of said end caps having a supporting surface that extends along and supports facing opposed vertebral surfaces of adjacent vertebrae; each of said end caps extending outwardly on opposed sides of a respective implant so as to provide support to the vertebrae during usage.

* * * * *